`US005771884A`

United States Patent [19]
Yarnall et al.

[11] Patent Number: 5,771,884
[45] Date of Patent: Jun. 30, 1998

[54] MAGNETIC EXHALATION VALVE WITH COMPENSATION FOR TEMPERATURE AND PATIENT AIRWAY PRESSURE INDUCED CHANGES TO THE MAGNETIC FIELD

[75] Inventors: Stephen T. Yarnall, Poway; David P. Winter, Encinitas; Bruce Van Wagner, Oceanside, all of Calif.

[73] Assignee: Nellcor Puritan Bennett Incorporated, Pleasanton, Calif.

[21] Appl. No.: 818,171

[22] Filed: Mar. 14, 1997

[51] Int. Cl.$^6$ ............................. A61M 16/00; A62B 7/00; A62B 9/04; F16K 1/08
[52] U.S. Cl. ............................... 128/205.24; 128/204.19; 137/908; 251/129.01; 251/129.1; 251/335.1; 251/335.2
[58] Field of Search ......................... 128/204.19, 205.24, 128/204.21, 204.18; 137/908; 251/65, 129.01, 129.05, 129.06, 129.09, 129.1, 335.1, 335.2

[56] References Cited

U.S. PATENT DOCUMENTS

| | | | |
|---|---|---|---|
| 4,624,282 | 11/1986 | Fargo | 251/129.1 |
| 4,930,541 | 6/1990 | Solberg | 251/129.1 |
| 5,072,729 | 12/1991 | DeVries | 128/204.23 |
| 5,108,070 | 4/1992 | Tominaga | 251/129.1 |
| 5,127,400 | 7/1992 | DeVries et al. | 128/205.24 |
| 5,339,807 | 8/1994 | Carter | 128/205.24 |
| 5,669,596 | 9/1997 | Yoshikawa et al. | 251/335.2 |

*Primary Examiner*—Kimberly L. Asher
*Attorney, Agent, or Firm*—Fulwider Patton Lee & Utecht, LLP

[57] ABSTRACT

The exhalation valve includes a valve housing with a valve seat having an annular shoulder, and a valve poppet having a face with a corresponding annular groove. A soft flexible diaphragm seal disposed between the face of the valve poppet and the valve seat provides a suspended soft seal, ensuring perpendicularity in the valve seal for improved accuracy of valve operation. An annular permanent magnet and an annular magnetic ring are disposed around and spaced apart from a magnetic body to define an air gap in which an electromagnetic coil is disposed. The electromagnetic coil is connected to a control mechanism by a flexible circuit connector that is sufficiently slack that provides minimal force transverse to the longitudinal axis of the valve. An assembly is provided for adjusting uniformity of the air gap and of concentricity of magnetic body and shaft of the poppet, and the control mechanism adjusts the current supplied to the electromagnetic coil, compensating for changes in the magnetic field strength of the valve due to changes in temperature, velocity of the valve poppet, and patient airway pressure. A flexible diaphragm is also connected between the valve poppet and magnetic body to prevent cross-contamination between the exhalation valve and breathing gas.

12 Claims, 3 Drawing Sheets

MAGNETIC EXHALATION VALVE WITH COMPENSATION FOR TEMPERATURE AND PATIENT AIRWAY PRESSURE INDUCED CHANGES TO THE MAGNETIC FIELD

BACKGROUND OF THE INVENTION

1. Field of the Invention

This invention relates generally to patient ventilators, and more particularly concerns a ventilator exhalation valve for regulating the release of breathing gas from an exhalation line of a patient ventilator.

2. Description of Related Art

Medical ventilators are generally designed to ventilate a patient's lungs with breathing gas to assist a patient in breathing when the patient is somehow unable to adequately breath without assistance. Pressure assistance can be instituted, for example, when the patient has already begun an inspiratory effort. With such a system, it is desirable to immediately increase the pressure after a breath is initiated in order to reach a target pressure. This rise in pressure causes flow to be initiated in the patient airway which supplies breathing gas t o the patient's lungs.

Conventional ventilators typically provide an option to maintain a slight "positive end expiration pressure" (PEEP) to help prevent collapse of the lungs of the patient, and regulate the patient proximal pressure during the expiration phase of breaths.

One type of ventilator exhalation valve is the electromechanical or solenoid-operated valve, controlling the valve by regulating the motion of a poppet in sealing a valve seat, providing control of back-pressure in a patient airway that is ideally proportional to current supplied by a control mechanism to the exhalation valve. In one conventional proportional electropneumatic solenoid-controlled valve, for example, an electromagnetic coil and a sleeve of magnetic steel contained within the coil provide a flux path for the magnetic field of the coil. A magnetic pole piece is contained within the bore of the solenoid, and a movable armature of magnetic material is supported within the bore by a pair of suspension springs. A valve portion connected to the solenoid includes a valve poppet attached to the armature assembly for controlling the opening and closing of the valve. The valve chamber receives fluid flow from inlet ports surrounding the outlet tube member, and a diaphragm is also provided as a flexible seal between the valve interior chamber and the moveable armature of the solenoid assembly to prevent foreign matter from the solenoid from entering the fluid in the valve.

Another conventional proportional solenoid device includes a movable armature assembly of magnetic material, substantially linear springs supporting the armature assembly, an electromagnetic coil, and an annular permanent magnet for producing a magnetic field of predetermined flux density in an adjustable trunk-polepiece of magnetic material in the center of the solenoid. Adjustment of the polepiece affects the flux gap between the polepiece and the armature, affecting the force applied by the armature.

In another known ventilator exhalation valve, a free-floating diaphragm is positioned in a valve housing adjacent to a valve seat, to allow flow in a forward direction from the patient through the valve, and to prevent reverse flow from the atmosphere to the patient. A valve poppet is positioned adjacent to the diaphragm for physically contacting the diaphragm to regulate the rate of flow through the valve, and a suspension assembly retains the valve poppet in position relative to the housing and diaphragm. A feedback assembly also provides a fixed velocity feedback signal via a flexible connector for the velocity of the valve poppet for dampening actuation of the armature due to turbulence of flow, with little dampening at low velocities, and greater dampening at high velocities. However, it would be desirable that such a flexible connector subject the valve to minimal side forces, to reduce friction in the operation of the valve. Conventional valves typically provide a generally fast response at high patient airway pressures; however, it would be desirable that actuation of the electromagnetic armature be compensated by taking into account patient airway pressure, to improve responsiveness of an exhalation valve at low pressures. It would also be desirable that actuation of the electromagnetic armature be compensated by taking into account changes in the magnetic field strength due to changes in temperature of the magnets, for optimizing pressure accuracy of the exhalation valve.

Improvements in reduction of friction in operation of the valve, such as by providing minimal side forces on the valve, and control of precise magnetic concentricity, would desirable. For improved operation of the valve at low pressures, it would also be desirable to provide a high degree of perpendicularity in the construction of the valve, and a valve seal requiring a low sealing force for improved accuracy of the valve. In addition, the surfaces of an exhalation valve that come in contact with patient breathing gases can become fouled, so that it would also be desirable that the valve poppet and seal be easily removable to facilitate their removal and replacement in the field. The present invention meets these needs.

SUMMARY OF THE INVENTION

Briefly, and in general terms, the present invention provides for an exhalation valve for a patient ventilator in which patient airway back pressure is proportional to current supplied to the exhalation valve, providing improved performance at low pressures compared to previously available valves. The poppet and surfaces that contact patient breathing gases are readily removable and replaceable, and a high degree of perpendicularity in the construction of the valve is obtained by a suspended soft valve seal requiring a low sealing force, for improved accuracy of the valve. Reduction of friction in operation of the valve is achieved by use of a flexible circuit connector to the electromagnetic coils, that imposes minimal side forces to the coil. The use of temperature compensation for the magnetic field strength, radial magnetic field strength averaging, perpendicularity control and variable velocity feedback relative to patient pressure improve the open control-loop accuracy capability of the valve and therefore provide for improved gas delivery accuracy, speed of response and over-pressure patient safety.

Accordingly, in one currently preferred embodiment, the invention provides for an exhalation valve for a patient ventilator having a patient airway for breathing gas, comprising a valve housing adapted to be connected to the patient ventilator, the valve housing having an exhalation line inlet port for receiving breathing gas from the patient airway, a valve seat on the inlet port, and an exhalation outlet port. A valve poppet is disposed in the valve adjacent to the valve seat, the valve poppet having a face with a surface defining an annular groove, and the valve seat having an annular shoulder corresponding to and adapted to interfit with the valve poppet annular groove. A soft flexible diaphragm seal is stretched over the face and periphery of the valve poppet, to provide a suspended soft seal for the exhalation valve requiring a low sealing force, and ensuring a high degree of perpendicularity in the valve seal, for improved accuracy of the valve.

The valve poppet has a generally cylindrical stem disposed in a generally cylindrical bore in a magnetic body disposed in the valve housing, and in a currently preferred embodiment, the valve poppet stem is suspended by a plurality of annular low friction bearings. An annular permanent magnet is disposed around the magnetic body for producing a magnetic field of predetermined flux density, and an annular magnetic ring adjacent to the annular permanent magnet is also disposed around the magnetic body for providing a flux path. The annular permanent magnet and the annular magnetic ring are spaced apart from the magnetic body so as to define an air gap.

An armature is disposed adjacent to the magnetic body having a central plate portion extending into the air gap and providing a substrate for an electromagnetic coil in the air gap and disposed between the magnetic ring and the magnetic body. A generally cylindrical bore is provided in the valve poppet stem, and the armature includes a cylindrical shaft having an upper portion extending within the central bore of the valve poppet stem, and a lower portion. In a currently preferred embodiment, the central plate portion and electromagnetic coil is connected to a control mechanism by a flexible connector that is sufficiently slack that the flexible connector provides minimal force transverse to the longitudinal axis of the valve. The valve housing includes a lower cap covering the armature and flexible connector of the valve, and the lower portion of the shaft is biased toward the valve seat by a spring supported by a spring rest mounted to the cap.

In a currently preferred embodiment, means are provided for adjusting the uniformity of the air gap and of concentricity of magnetic body. The magnetic body preferably includes an outwardly extending alignment ring portion defining a lower shoulder portion against which the valve housing abuts, and a lock nut preferably has a right angle inner collar that engages an opposing side of the alignment ring of the magnetic body, to position the magnetic body in the valve, and to position the poppet to be concentric in the valve and perpendicular to the valve seat.

In a currently preferred embodiment, a variable velocity feedback assembly is provided that includes a permanent magnet disposed in the lower shaft portion of the armature, and a passive stationary velocity coil mounted to the cap and disposed around the permanent magnet in the lower shaft portion of the armature for providing an electrical signal indicative of velocity and direction of the valve poppet to the control mechanism.

The control mechanism preferably also receives pressure signals indicative of the proximal pressure, and adjusts the current supplied to the electromagnetic coil, compensating for changes in the magnetic field strength of the valve due to changes in temperature, velocity of the valve poppet, and patient airway pressure.

In another currently preferred embodiment, the exhalation valve includes a temperature sensor connected to provide temperature signals indicative of the temperature of the valve magnet to the control mechanism, and the control mechanism adjusts the current supplied to the main electromagnetic coil based upon the temperature signals and a predetermined thermal coefficient of magnetic strength of the valve.

In another currently preferred embodiment, a flexible diaphragm is connected between the valve poppet and magnetic body to prevent cross-contamination between the exhalation valve and breathing gas.

These and other aspects and advantages of the invention will become apparent from the following detailed description and the accompanying drawings, which illustrate by way of example the features of the invention.

DETAILED DESCRIPTION OF THE PREFERRED EMBODIMENTS

Figure 1:
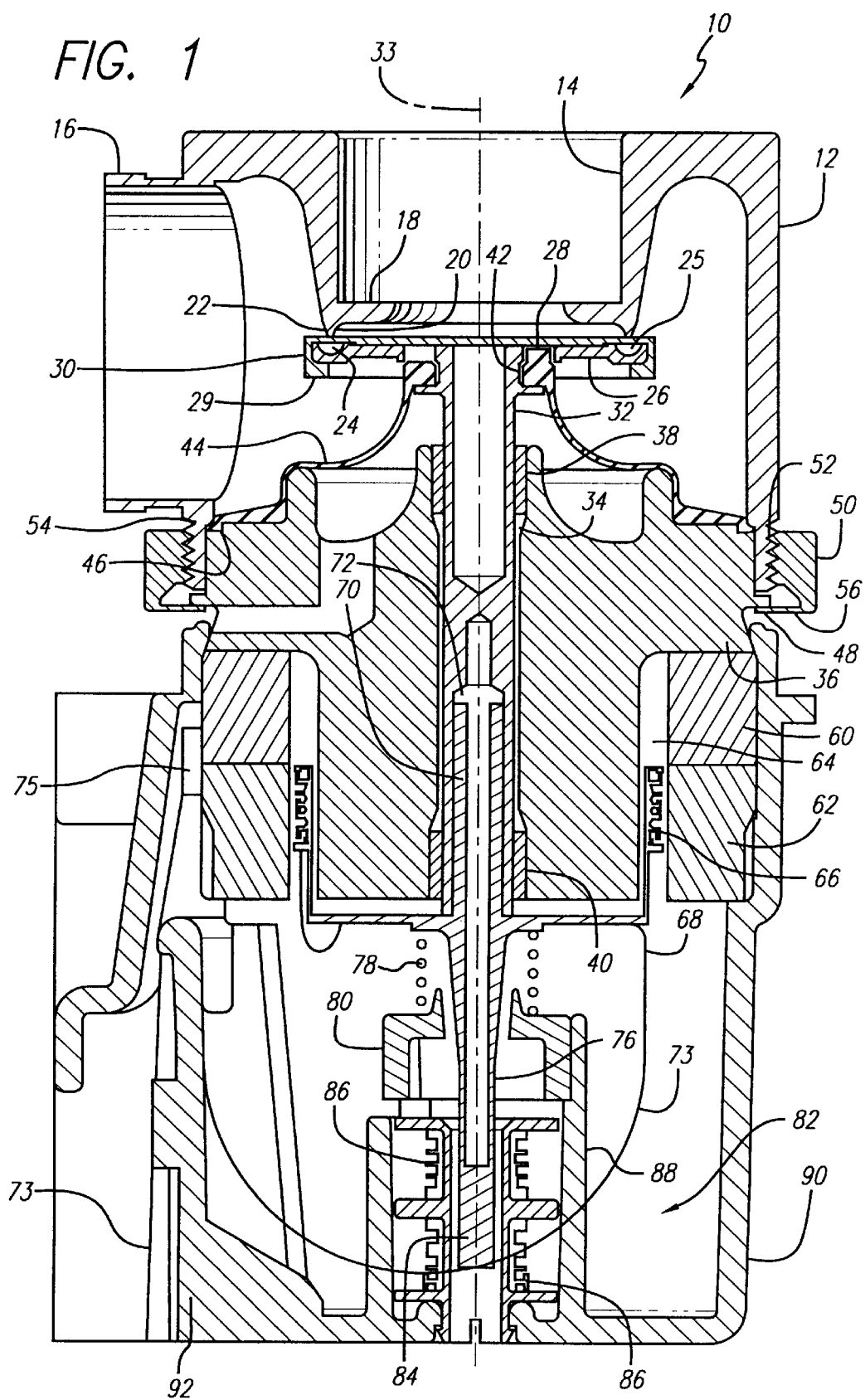
FIG. 1 is a sectional, schematic diagram of the exhalation valve of the invention.
Figure 2:
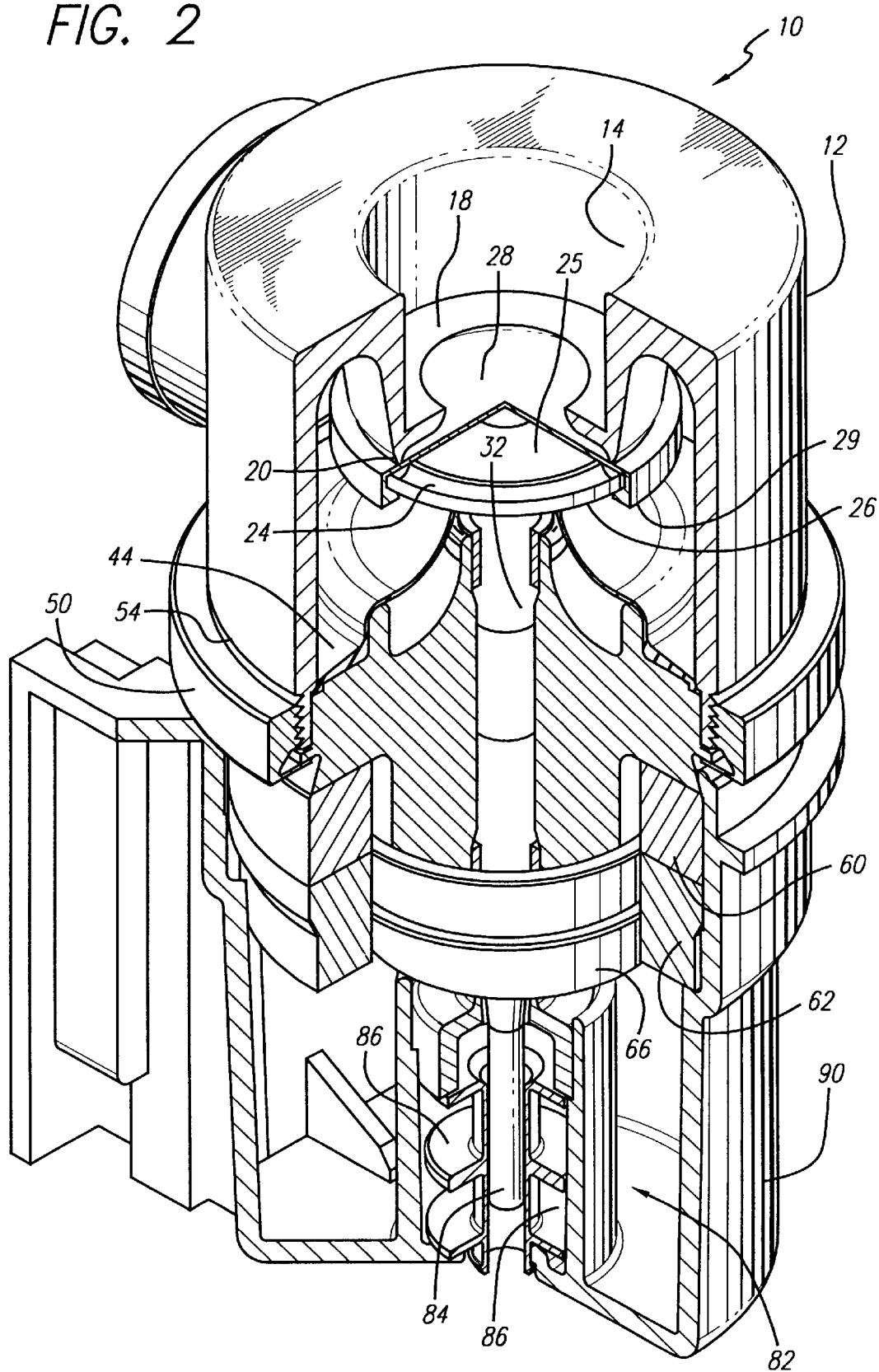
FIG. 2 is a cutaway perspective view of the exhalation valve of FIG. 1.
Figure 3:
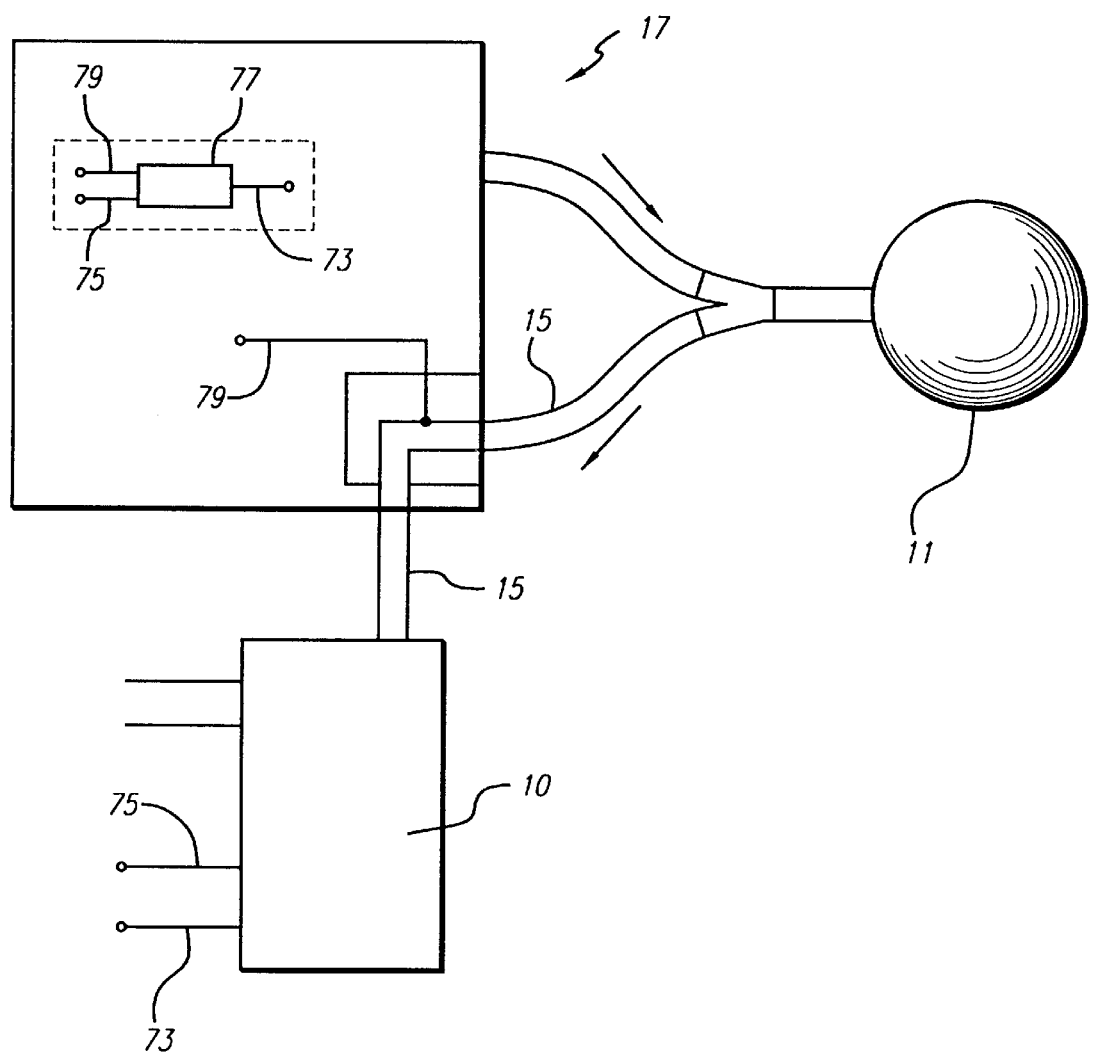
FIG. 3 is a schematic diagram of the exhalation valve of FIG. 1 in a patient ventilator system.

Performance of exhalation valves can be hindered, particularly at low patient proximal pressures, by problems of the sealing force of the valve, and friction in operation of the valve, such as can be caused by side forces on the valve, imprecise magnetic concentricity, and the degree of perpendicularity of the valve seal. In addition, the surfaces of an exhalation valve that come in contact with patient breathing gases can become fouled. The performance of an exhalation valve can also be affected by changes in the patient proximal pressure, and changes in the magnetic field strength due to changes in temperature of the magnets.

As is illustrated in the drawings, the invention is embodied in an exhalation valve 10 for a patient ventilator for a patient 11, having a valve housing 12 that is currently preferably made from aluminum, although other similar materials, such as stainless steel or plastics, may be suitable. The valve housing includes an exhalation line inlet port 14 adapted to be connected to a patient airway exhalation line 15 of the patient ventilator 17, and an exhalation outlet port 16. The inlet port includes an interior flange 18 limiting the mating of the inlet port to an access port of the patient airway of the ventilator. The inlet port includes a valve seat 20 adjacent to the flange, and formed with an apical annular shoulder 22. A correspondingly shaped annular groove 24 adapted to receive and mate with the apical annular shoulder of the valve seat is formed in the face 25 of the valve poppet 26 disposed in the valve body adjacent to the valve seat. A soft flexible seal 28 is preferably placed between the apical annular shoulder of the valve seat and the annular groove of the poppet, and preferably includes an outer flange 29 that snaps over the periphery 30 of the poppet to stretch the soft flexible seal over the face of the poppet, to require a low force to seal the valve. The soft flexible seal is currently preferably formed of silicone rubber, although other similar rubbers and elastomeric materials may also be suitable.

The poppet includes a valve poppet shaft 32 extending perpendicular to the face of the poppet along the longitudinal axis 33 of the valve, and is disposed in a generally cylindrical bore 34 of a magnetic body 36. The magnetic body is currently preferably formed of magnetic stainless steel, although other magnetic materials not retaining a permanent magnetic field, such as magnetic iron, for example, may also be suitable. The valve poppet shaft is currently preferably mounted and suspended within the bore of the magnetic body by an annular bearing 38 disposed in one end of the bore of the magnetic body, and another annular bearing 40 disposed in the other end of the bore of the magnetic body, although other numbers of annular bearings serving to suspend the valve poppet shaft within and uniformly spaced apart from the interior of the bore of the magnetic body could also be used. The annular bearings are preferably formed of a low friction material, and are currently typically made of 35% carbon fiber filled polyetherether ketone (PEEK). A notch 42 is provided in the valve poppet shaft near the poppet in which an annular isolation diaphragm 44 is centrally secured, covering the magnetic body and secured thereto at an upper shoulder 45 of the magnetic body, for isolating the interior of the valve from the patient airway, to prevent cross-contamination between the valve and the breathing gas in the airway.

Means for adjusting the positioning of the magnetic body and shaft of the poppet in the valve include an outwardly extending alignment ring 46 of the magnetic body defining a lower shoulder 48 against which the valve housing abuts, and a lock nut 50 having internal threads 52 that engage external threads 54 on the valve housing. The lock nut preferably has a right angle inner collar 56 that engages the lower shoulder of the alignment ring of the magnetic body. Tightening of the lock nut on the alignment ring thus provides perpendicularity of the alignment of the shaft of poppet valve, the bearings, the magnetic body, and the poppet with respect to the valve seat.

An annular permanent magnet 60, which is currently preferably a rare earth permanent magnet, and a magnetic ring 62 made of magnetic material, and typically formed of iron or magnetic steel, are disposed in the valve around and spaced apart from the magnetic body, so as to define an air gap 64 therebetween. An electromagnetic coil 66 is uniformly disposed around the magnetic body in the air gap, mounted on a support surface of an armature 68 that extends uniformly into the air gap. The armature has an upper cylindrical shaft 70 extending longitudinally into a longitudinal cylindrical bore 72 of valve poppet shaft. A slack flexible circuit connector 73 is secured to the armature and is electrically connected between the electromagnetic coil and a control mechanism 74 providing controlled supply of current to the electromagnetic coil, and exerting minimal side forces on the armature of the valve as the armature and valve poppet move within the valve. The radial magnetic field strength of the exhalation valve is averaged by the structure of the magnet, magnetic body and magnetic ring. By ensuring uniformity of the air gap, and precise magnetic concentricity, hysteresis of the exhalation valve is minimized. The low sealing force required to close the valve is generally proportional to the current supplied to the electromagnetic coil, and is generally unaffected by the displacement of the valve poppet.

The control mechanism preferably includes a microprocessor based computer control unit 77 that receives input signals from a pressure sensor 79 monitoring proximal pressure in the patient airway, and from a temperature sensor such as thermistor 75 disposed in the exhalation valve adjacent to the magnet and magnetic ring. Since the magnetic subassembly of the exhalation valve has a thermal coefficient of magnetic strength, typically on the order of 0.1%/°C., so that the magnetic strength of the valve decreases as temperature increases, the control mechanism adjusts the amount of current supplied to the electromagnetic coil based upon the temperature signal from the temperature sensor.

In addition, the control mechanism adjusts the current according to the monitored pressure in the patient airway as is described in U.S. Pat. No. 5,339,807, which is specifically incorporated herein in its entirety by reference. The armature also includes a lower armature shaft 76 supported by a spring 78 mounted on the spring rest 80 adjacent to the variable velocity feedback assembly 82. The variable velocity feedback assembly includes a velocity magnet 84, which is a permanent magnet, disposed in the lower armature shaft, in a bore spaced apart from passive stationary velocity coils 86 located in the velocity coil housing 88 of the lower cap 90 covering the magnet, magnetic ring and flexible connector. A cap door 92 is also typically provided in the cap for access to the flexible circuit connector and thermistor of the valve.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An exhalation valve for a patient ventilator having a patient airway for breathing gas, comprising:

a valve housing adapted to be connected to the patient ventilator, said valve housing having an exhalation line inlet port for receiving breathing gas from the patient airway, a valve seat on said inlet port, and an exhalation outlet port;

a valve poppet disposed in said valve housing adjacent to said valve seat, said valve poppet having a longitudinal shaft and a face perpendicular to the shaft with a surface defining an annular groove, and said valve seat having an annular shoulder corresponding to and adapted to interfit with said valve poppet annular groove;

a magnetic body disposed in said valve housing having a generally cylindrical longitudinal bore, said valve poppet shaft being disposed in said generally cylindrical longitudinal bore in said magnetic body, said valve poppet shaft being suspended in said generally cylindrical longitudinal bore in said magnetic body by a plurality of annular low friction bearings;

an annular permanent magnet disposed around said magnetic body for producing a magnetic field of predetermined flux density;

an annular magnetic ring disposed around said magnetic body adjacent to said annular permanent magnet for providing a flux path, said annular permanent magnet and said annular magnetic ring being spaced apart from said magnetic body so as to define an air gap therebetween;

an armature disposed adjacent to said magnetic body having a central plate portion extending into said air gap, said armature including an electromagnetic coil disposed on said armature central plate portion in said air gap between said magnetic ring and said magnetic body, said valve poppet shaft having a generally cylindrical longitudinal bore, said armature including a cylindrical longitudinal shaft having an upper portion extending within said central bore of said valve poppet shaft, and a lower portion;

a control mechanism for supplying current to said electromagnetic coil for causing an axial force for axial movement of said poppet with respect to said valve seat; and means for positioning said magnetic body relative to said valve housing.

2. The exhalation valve of claim 1, further comprising a soft flexible diaphragm seal disposed between said valve seat and said face of said valve poppet.

3. The exhalation valve of claim 1, wherein said electromagnetic coil is connected to said control mechanism by a flexible connector that is sufficiently slack that said flexible connector provides minimal force transverse to said longitudinal axis of said valve.

4. The exhalation valve of claim 3, wherein said valve housing includes a lower cap covering said armature and said flexible connector of said valve, and said lower portion of said shaft is biased toward said valve seat by a spring supported by a spring rest mounted to said cap.

5. The exhalation valve of claim 1, wherein said means for positioning said magnetic body comprises external threads on a portion of the valve housing, and a lock nut having corresponding internal threads for engaging said external threads on said valve housing.

6. The exhalation valve of claim 5, wherein said magnetic body comprises an outwardly extending alignment ring, said valve housing abutting against a surface of said alignment ring, and said lock nut preferably has a right angle inner collar that engages an opposing side of said alignment ring of said magnetic body, to position said magnetic body and said poppet suspended therein so as to position said shaft of said poppet to be perpendicular to said valve seat.

7. The exhalation valve of claim 1, further comprising a variable velocity feedback assembly for providing an electrical signal indicative of velocity and direction of said valve poppet to said control mechanism.

8. The exhalation valve of claim 7, wherein said variable velocity feedback assembly comprises a permanent magnet disposed in said lower shaft portion of said armature, and a passive stationary velocity coil mounted to said cap and disposed around said permanent magnet in said lower shaft portion of said armature for providing an electrical signal indicative of velocity and direction of said valve poppet to said control mechanism.

9. The exhalation valve of claim 1, wherein said exhalation valve includes a temperature sensor connected to provide temperature signals indicative of the temperature of said valve to said control mechanism, and said control mechanism adjusts the current supplied to said main electromagnetic coil based upon said temperature signals and a predetermined thermal coefficient of magnetic strength of said valve.

10. The exhalation valve of claim 9, wherein said control mechanism receives pressure signals indicative of the proximal pressure, and adjusts the current supplied to said electromagnetic coil, compensating for changes in the magnetic field strength of said valve due to changes in temperature, velocity of said valve poppet, and patient airway pressure.

11. The exhalation valve of claim 1, further comprising a flexible diaphragm connected between said valve poppet and magnetic body to prevent cross-contamination between said exhalation valve and breathing gas.

12. The exhalation valve of claim 1, wherein a sealing force of said valve poppet is generally proportional to said current supplied to said electromagnetic coil, and is generally unaffected by displacement of said valve poppet.

* * * * *